United States Patent [19]

Powell

[11] Patent Number: 4,517,844

[45] Date of Patent: May 21, 1985

[54] FLUID DAMPING DEVICE FOR A COMPLIANT SYSTEM

[76] Inventor: Steven Powell, 341 W. Harding, Lombard, Ill. 60148

[21] Appl. No.: 500,940

[22] Filed: Jun. 3, 1983

[51] Int. Cl.³ .......................... A61B 5/02; G01L 19/00
[52] U.S. Cl. ...................................... 73/707; 73/756; 128/672
[58] Field of Search .................. 73/707, 756; 128/672, 128/673, 674, 675, 748; 137/269; 251/118

[56] References Cited

U.S. PATENT DOCUMENTS 3,665,948 5/1972 Hohberger ............................ 73/707
4,335,729 6/1982 Reynolds et al. ..................... 73/707

Primary Examiner—Donald O. Woodiel
Attorney, Agent, or Firm—Emrich & Dithmar

[57] ABSTRACT

Apparatus for removing undesirable resonance in a closed, tubular fluid flow system permitting more accurate transducer measurement of varying fluid pressure within the system is disclosed. The apparatus includes a compliant air cavity coupled to the system via a small diameter aperture, or passage. The cavity is within an elongated pipe, or tube, the proximal end of which is inserted in a conventional cylindrical sleeve and includes the small diameter passage for coupling the air cavity to the fluid system. A plurality of such elogated tubes, each having a predetermined length and thus a predetermined cavity size, are provided for selective insertion in the cylindrical sleeve for providing the fluid flow system with a fixed series hydraulic resistance and an incrementally variable parallel hydraulic capacitance for matching the hydraulic impedance of the system. The elongated tubes may be color-coded to facilitate proper tube selection for optimum impedance matching in providing for the selective suppression of undesirable system resonance and associated improved transducer frequency response. The apparatus of the present invention is particularly adapted for use in a catheter-tubing-transducer system as used in electromanometry systems and permits a varying hemodynamic pressure to be more accurately measured and recorded.

10 Claims, 6 Drawing Figures

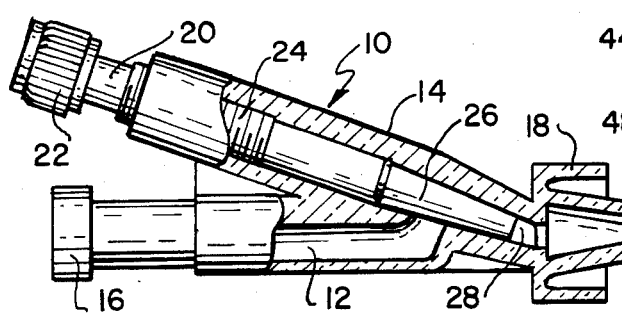
FIG. 1
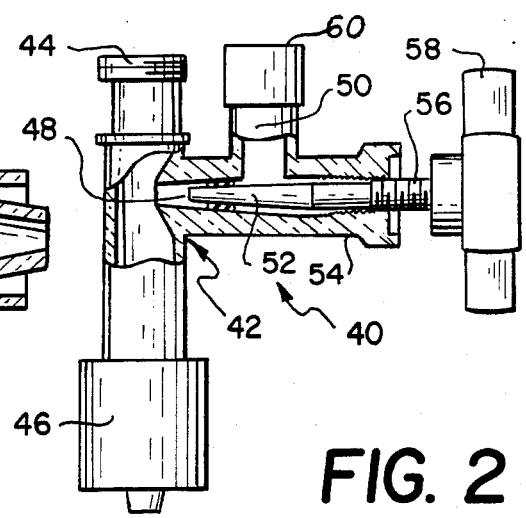
FIG. 2
(PRIOR ART)
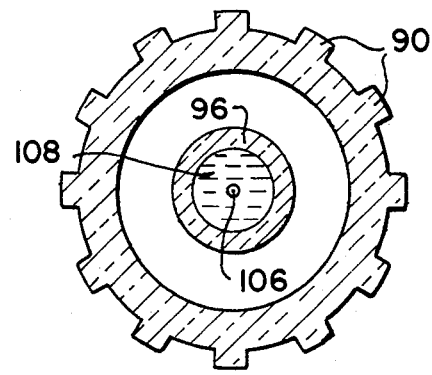
FIG. 6
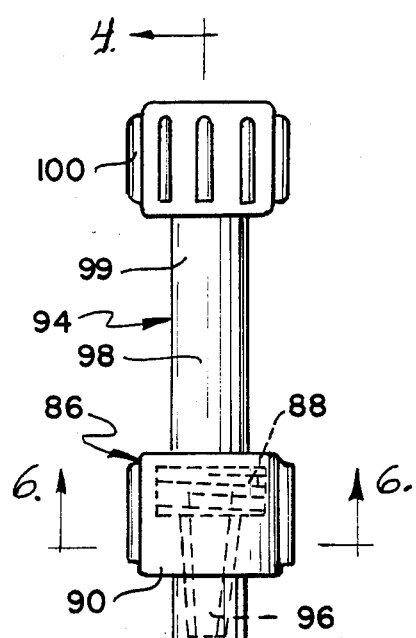
FIG. 3
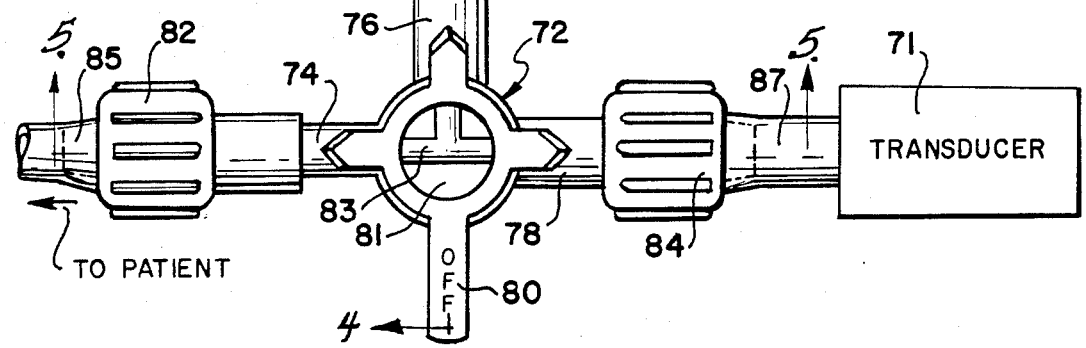

FLUID DAMPING DEVICE FOR A COMPLIANT SYSTEM

BACKGROUND OF THE INVENTION

The present invention relates in general to closed fluid flow systems and is particularly directed to the accurate measurement of a variable pressure in a catheter-tubing-transducer system by damping out system resonance.

The catheter-tubing-transducer system typically used in various health-related applications is an underdamped, second-order, dynamic fluid system similar to a bouncing tennis ball. The catheter, which is inserted into a patient, and tubing are filled with a liquid, typically a saline solution, to permit hemodynamic pressures to be transmitted as pressure pulses through the liquid-filled catheter. The pressure waves propagated in the system due to a patient's heartbeat have a characteristic frequency, with the propagation of these waves related to the system's inherent damping coefficient. In terms of mechanical parameters, this type of second-order system can be described in terms of three parameters: elasticity, mass and friction. Elasticity refers to the stiffness of the system, normally caused by the flexibility of the transducer diaphragm. This elasticity can be changed by air bubbles, compliant tubing, or other elastic elements in the system. The mass of the system is the fluid mass moving in the catheter and interconnecting tubing. Frictional forces arise at the inner surface of the catheter and tubing as the fluid within is displaced with each pulsating change in blood pressure. In this type of underdamped, second-order system, the aforementioned three system parameters determine two measurable parameters, i.e., the system's natural frequency and damping coefficient. The natural frequency refers to how rapidly the system oscillates, while the damping coefficient refers to how quickly the system comes to rest.

Frequently it is necessary, particularly in the case of one who is critically ill, to continually and accurately monitor a patient's heartbeat and blood pressure characteristics. Electromanometry systems for monitoring and recording hemodynamic pressures are gaining increasing importance in modern medicine. These systems transform hemodynamic pressures into observable and recordable electronic waveforms representing the periodic pulsations of blood transmitted as pressure pulses through the liquid-filled catheter to a transducer. From the parameters thus measured and recorded, important diagnostic data concerning a patient's condition is made available.

In this type of system, yet another system parameter, the frequency bandwidth of the system, must be considered. The system's frequency bandwidth provides an indication of the accuracy of the pressure readings, with a high bandwidth representing a fast system response capable of providing accurate and reliable hemodynamic pressure measurements. Those systems with the best dynamic response are those having a high natural frequency which allows for great latitude in system damping coefficient. However, compliance in the system, such as introduced by a small air bubble, increases the damping coefficient and decreases the natural frequency. In addition, these systems possess a characteristic resonance which results in a tendency to amplify pulsations in the region of the system's natural resonant frequency much more than pulsations having other frequencies. This results in a form of distortion in measuring the pulsating waveforms known as "harmonic ringing". The resonance of this type of closed fluid flow system seriously degrades the accuracy of pressure variation measurements in such systems.

The prior art discloses various attempts to compensate, or correct, for the characteristic resonance of an electromanometry system. These approaches have included electrical compensation systems which are generally expensive and complicated. Other approaches have employed hydraulic damping devices with varying degrees of success.

One such approach which makes use of a variable series hydraulic resistance in the system is shown in FIG. 1. This device 10 is coupled in the system between the transducer and a flush device by means of first and second couplers 16, 18, where fluid flow is from left to right in FIG. 1. The device includes main tubing 12 to which is securely coupled, so as to be integral with, a housing 14 with an inlet port and an interior throughbore. Inserted by means of threads within interior throughbore is a threaded shaft 20 having at one end a knob 22 and an opposite leading tapered end 26 which terminates in tip 28. By rotating knob 22, shaft 20 may be longitudinally displaced along the interior of cylindrical housing 14 to permit tip 28 to be selectively positioned relative to the fluid flow. By selectively varying the series resistance in the system, the damping therein may be controlled for reducing resonances therein. This approach, however, results in reduced high frequency response and limited system measurement accuracy.

Another approach is described in U.S. Pat. No. 4,335,279 to Reynolds et al involving a variable parallel capacitance damping approach as shown in FIG. 2 herein. This device 40 includes a plastic T-coupling member 42, to the opposite ends of which are respectively coupled conventional female and male luer fittings 44, 46. Female luer fitting 44 is in the direction of a transducer (not shown), while male luer fitting 46 is in the direction of the patient. The T-coupling member 42 includes a cylindrical housing 54 having a threaded interior throughbore and is coupled to the main tubing by means of an inlet port 48. A side port 50 with an end cap 60 is coupled to the housing 54, in which the threaded shaft 56 is positioned by means of engaging threads. Shaft 56 includes a knob 58 for the rotation thereof. A compliant air cavity is provided on the interior of side port 50 and is connected through a variable impedance device, i.e., shaft 56 with leading tapered end 52, which is coupled in parallel to the liquid-filled catheter of the electromanometry system. By varying the hydraulic impedance through which the compliant air cavity is coupled to the system, the characteristic impedance of the system may be matched. The purpose of the invention is to provide a wide range of control for purposes of hydraulically matching the characteristic impedance of an electromanometry system. This approach, however, provides the parallel capacitance with only limited system isolation and requires a rather complicated, continuously adjustable device which increases the cost of these systems. U.S. Pat. No. 3,665,948 to Hohberger, while not intended to reduce or eliminate hydraulic resonance in a fluid flow system, discloses an apparatus for limiting the magnitude of transient hydraulic pressure waves in such a system.

The present invention overcomes the aforementioned limitations of the prior art by providing a fluid damping device for a compliant system which substantially eliminates resonances in the system permitting accurate pressure measurements to be made. In addition, the present invention is inexpensive, easily implemented, and compatible with conventional catheter-tubing-transducer configurations typically encountered in electromanometry systems.

SUMMARY OF THE INVENTION

Accordingly, it is an object of the present invention to provide for more accurate measurement of pressure variations in a closed, compliant, fluid flow system such as comprised of a catheter, tubing and a transducer by the selective damping out of system resonances.

The present invention contemplates the selective coupling of an air cavity of predetermined volume to an electromanometry system having a given set of fluid flow characteristics and typically comprised of a catheter, tubing and transducer for providing for more accurate measurement of pressure variations within the system by removing unwanted resonance therefrom. One of a plurality of elongated, color-coded pipes, or tubes, each having an internal cavity of predetermined size coupled to the proximal end of the tube via a small diameter orifice, is selectively coupled into the system via an inlet port. The volume of this air cavity represents a parallel hydraulic capacitance, while the diameter and length of the orifice represents a series hydraulic resistance with respect to the fluid system. Changing the length of the pipe varies the parallel capacitance and by proper selection of the diameter and length of the orifice the impedance of the fluid flow system may be precisely matched in providing more accurate pressure measurements over a wide range of catheter-tubing-transducer configurations. Thus, a predetermined number of elongated tubes of various lengths will provide a corresponding number of matching hydraulic impedance values, each capable of damping the resonant frequencies of a closed fluid flow system of selected characteristics, or dimensions.

BRIEF DESCRIPTION OF THE DRAWINGS

The appended claims set forth those novel features believed characteristic of the invention. However, the invention itself as well as further objects and advantages thereof, will best be understood by reference to the following detailed description of a preferred embodiment taken in conjunction with the accompanying drawings, where like reference numerals are used to designate like elements throughout the various figures, in which:

FIG. 1 illustrates a prior art hemodynamic damping device employing a variable series hydraulic resistance;

FIG. 2 is illustrates a prior art hemodynamic damping device utilizing a variable series hydraulic resistance in combination with a fixed parallel hydraulic capacitance;

FIG. 3 is a partially cut away elevational view of a fluid damping device for a compliant system in accordance with the present invention;

FIG. 6 is a sectional view taken along sight line 6—6 of FIG. 3.

DESCRIPTION OF THE PREFERRED EMBODIMENT

Figure 4:
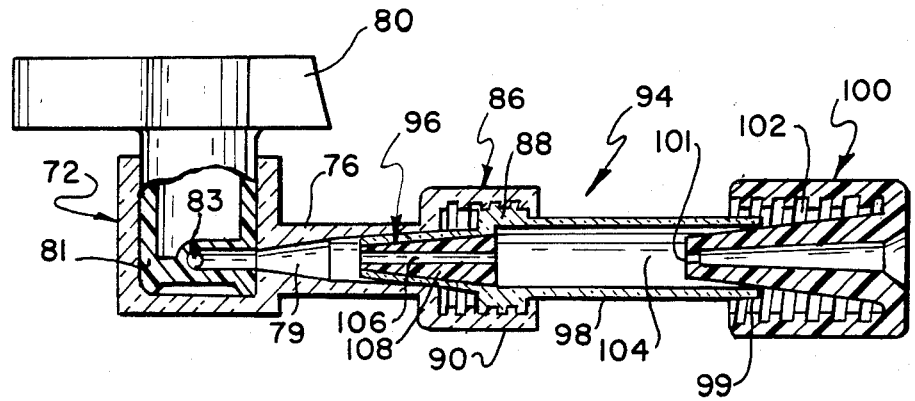
FIG. 4 is a sectional view of the fluid damping device of FIG. 3 taken along sight line 4—4 therein.
Figure 5:
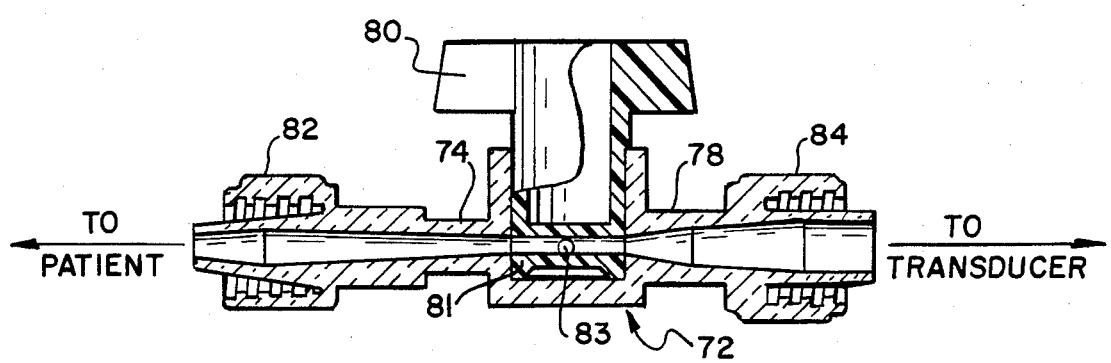
FIG. 5 is a sectional view of the fluid damping device of FIG. 3 taken along sight line 5—5 therein.

Referring to FIG. 3, there is shown a partially cut away elevational view of a fluid damping device 70 for a compliant system in accordance with the present invention. The device is comprised primarily of a parallel hydraulic capacitance device 94 and means for coupling the parallel capacitance device into an electromanometry system which typically would include a catheter, tubing (not shown), and a transducer 71 for measuring pressure changes in the fluid contained within the catheter and tubing. The catheter and tubing, which are not shown for the sake of simplicity and because they do not form a part of the present invention, are filled with a liquid, typically a saline solution, to permit hemodynamic pressures to be transmitted as pressure pulses through the liquid-filled catheter. The present invention is not disclosed in terms of the particulars of such a catheter-tubing-transducer combination, since conventional means are utilized for coupling the present invention into such a system.

As used herein, impedance means a hydraulic resistance and/or a hydraulic reactance. The reactive component of the impedance may be derived either from a compliance or from the inertia of the system. The inertia of the system is determined by the fluid density, the effective length of the system and by the area of a hydraulic restriction. The reactance is due to the system's compliance, or the ability of the system to elastically yield to variations in internal fluid pressure.

A conventional multi-position stopcock 72 is used to connect the parallel capacitance device 94 into a catheter-tubing-transducer system. Stopcock 72 includes first, second and third connecting tubes 74, 76 and 78, coupled thereto and integral therewith. The housing of the stopcock 72 includes a rotary control knob 80 integral with a rotatable housing 81 within stopcock 72 for selectively aligning passages 83 within housing 81 relative to the first, second and third tubes 74, 76 and 78 as desired. Integral with and positioned upon the distal end portions of first and third tubes 74, 78 are respective threaded coupling members 82, 84, shown as male luer fittings. Coupling members 82, 84 may be connected in a conventional manner to complementary threaded fittings on the ends of respective tubing sections 85, 87 in an electromanometry system. In a typical installation, male coupling member 82 would be proximally located with respect to the patient being monitored by the system, while male coupling member 84 would be proximally positioned with respect to the transducer 71 measuring the patient's blood pressure.

The parallel capacitance device 94 may be inserted in and connected to the female coupling member 90 of a threaded coupler 86 in a conventional manner. The parallel capacitance device 94 is in the form of an elongated, tubular pipe having a tapered proximal end 96, an intermediate tubular section 98, and an open distal end 99. Positioned upon distal end 99 is an end cap 100 which serves to seal the distal end 99 of the parallel capacitance device 94 while affording a gripping means for grasping the parallel capacitance device 94 in inserting and removing it from the threaded coupler 86 connected to the stopcock assembly 72 via second tube 76. As shown in FIG. 3, the parallel capacitance device 94 is oriented 90° with respect to the fluid flow from the patient to transducer 71. Positioned on the proximal end 96 of the parallel capacitance device 94 is a threaded male portion 88 for securely engaging the threaded female portion 90 of threaded coupler 86.

Referring to FIG. 4 which is a sectional view of the fluid damping device of FIG. 3 taken along sight line 4—4 therein, there is shown in greater detail the parallel capacitance device 94 of the present invention. The tapered proximal end 96 of the parallel capacitance device 94 includes a cylindrical spacer 108 positioned along the length thereof which includes an air passage 106 extending the length and through the center thereof. The inner portion of the tapered proximal end 96 has a diametrally reduced cross sectional area in proceeding toward the end of the capacitance device 94. Positioned immediately adjacent the tapered proximal end 96 is the intermediate tubular section 98 which includes a compliant air cavity 104 internal thereto. The compliant air cavity 104 extends substantially the entire length of the tubular section 98 and is sealed on the distal end 99 thereof by means of end cap 100. End cap 100, in a preferred embodiment, includes a threaded, internal portion 102 and a center, plug-like structure 101 which facilitates the secure engagement of end cap 100 on the distal end 99 of the parallel capacitive device 94.

When coupled to a fluid-filled system of tubes including the stopcock assembly 72 as shown in FIG. 3, the cavity 104 in parallel-capacitance damping device 94 will be filled with trapped air. In addition, trapped air will be present within passage 106 extending along the length and in the center of the tapered proximal end 96 of the parallel capacitance device 94. Thus, air will be trapped within cavity 104 and passage 106 when the parallel capacitance device 94 is coupled to the stopcock assembly 72 as shown in FIGS. 3 and 4. The air within passage 106 acts as a series hydraulic resistance with respect to the fluid in stopcock 72 and associated tubing system. Similarly, compliant air cavity 104 will act as a parallel hydraulic capacitance with respect to the fluid flow system. The resistance is determined by the diameter and length of the air passage 106, while the parallel capacitance is determined by the volume of the compliant air cavity 104. The compliant air cavity 104 permits alternating pressure pulses to pass through the impedance provided by passage 106. Thus, the present invention operates in a static mode and provides a hydraulic impedance which may be selectively varied over a wide range, as explained in the following paragraphs, for the purpose of accurately matching the characteristic impedance of a wide variety of catheter-tubing-transducer systems. With the impedance of the system thus matched, unwanted resonance may be substantially reduced in the system permitting more accurate pressure measurements to be made.

The present invention contemplates varying the volume of the compliant air cavity 104 in a step-wise manner so as to provide selective impedance matching for the fluid flow system in which the parallel capacitance device 94 is inserted. For example, by having a number of parallel capacitance devices 94 each having a tubular section 98 of different length, the impedance of a wide variety of tubular fluid flow systems may be precisely matched. Since the flexible tubing utilized in most electromanometry systems is of standard lengths, a limited number of parallel capacitive devices 94, each of a corresponding different length, would be required for impedance matching purposes. The fixed resistance provided by air passage 106 isolates the selective, step-wise variable, impedance of the compliant air cavity 104 from the fluid flow system so as to maintain a high frequency response while substantially eliminating resonance from the system. This provides for more accurate fluid pressure measurements without continuously adjusting the system for impedance matching purposes. The inherent inaccuracies and errors in this type of continuous, manual adjustment approach are thus eliminated in the present invention.

In a preferred embodiment, the cylindrical spacer portion 108 of the parallel capacitive device 94 may be color-coded to indicate the hydraulic impedance value it possesses for impedance matching purposes. Thus, with the tube length of the fluid flow system known, one would merely have to select the appropriate color-coded impedance matching device for insertion in the system in providing precise impedance matching therein.

As shown in FIG. 6, which is taken along sight line 6—6 of FIG. 3, the air passage 106 is of small diameter and is located essentially in the center of tapered proximal end 96 and the cylindrical spacer 108 positioned therein. The small diameter of air passage 106 precludes fluid flow therethrough and into the cavity 104, while permitting air to be trapped and, to a limited extent, compressed within compliant air cavity 104. Matching the impedance of cavity 104 with that of the fluid flow system permits those waves propagated at the resonant frequency of the system to be substantially dampened and thus dissipated and removed therefrom to permit more accurate pressure measurements. Stopcock assembly 72 and parallel capacitance device 94 may be comprised of any conventional thermoplastic or ceramic material. For extremely precise applications, the tapered proximal end 96, including the cylindrical spacer 108, and the intermediate tubular section 98 of the parallel capacitance device 94 may be comprised of a metal, such as stainless steel, for providing a highly accurate, fixed matching impedance.

There has thus been shown a fluid damping device for a compliant system such as comprised of a catheter, tubing and transducer, which provides a step-wise variable, parallel hydraulic capacitance coupled to the system via a fixed series hydraulic resistance for precise system impedance matching in removing unwanted resonance from the fluid flow system permitting more accurate measurement of pressure, and pressure variations, therein. The incrementally variable, parallel capacitance is provided by a plurality of elongated, tube-like structures, each containing a compliant air cavity coupled to the fluid flow system via a small diameter air passage. The length of the tube-like member may be selectively varied to change its impedance in a step-wise manner for impedance matching in systems of different flexible tube lengths. Each tube-like member may be color-coded to indicate its impedance value for error-free impedance matching.

While particular embodiments of the present invention have been shown and described, it will be obvious to those skilled in the art that changes and modifications may be made without departing from the invention in its broader aspects. For example, while changes in the volume of the air cavity forming the parallel hydraulic capacitance have been described in terms of changes in the length of the parallel capacitance device, it would be obvious to one skilled in the art that this could as easily be accomplished by varying the width, or diameter, of the parallel capacitance device. Changes in the length of this device have been emphasized in the present application because the plastic or ceramic tube-like structures from which one embodiment of the parallel capacitive device could be made are typically of a uniform, conventional inner and outer diameter. Thus, it would be more economical to change the length of the tube-like structure to provide the aforementioned variable impedance matching capability. In addition, while the parallel capacitance device of the present invention has been shown as securely coupled to a compliant fluid flow system by means of a threaded coupling for increased safety, the parallel capacitance device may be provided without threads and merely inserted in a non-threaded aperture in the compliant fluid flow system where appropriate.

Therefore, the aim in the appended claims is to cover all such changes and modifications as fall within the true spirit and scope of the invention. The matter set forth in the foregoing description and the accompanying drawings is offered by way of illustration only and not as a limitation. The actual scope of the invention is intended to be defined in the following claims when viewed in their proper perspective based on the prior art.

I claim:

1. In a compliant fluid flow system including flexible tubing of a fixed length, said system having a characteristic hydraulic impedance determined by the length of said tubing and including pressure sensitive means for measuring the pressure in said system, apparatus for increasing the accuracy of said pressure measurements by compensating for the resonance of said system, said apparatus comprising:

an inlet port coupled to said fluid flow system;

a plurality of elongated tubes each having a proximal end, a distal end and a predetermined length and including:

an internal structure defining a cavity therein with the volume of said cavity increasing with increasing tube length;

first sealing means located on the distal end of said tube for forming a closure therefor; and second sealing means located on the proximal end of said tube for forming a partial closure having a fixed resistance wherein when the proximal end of a designated tube is inserted in said inlet port, a compliant air cavity having a characteristic impedance determined by the volume of said cavity is formed such that the resonance of said system may be compensated for by insertion in said inlet port of the one of said plurality of elongated tubes having an impedance which matches the characteristic impedance of said fluid flow system.

2. An apparatus in accordance with claim 1 wherein each of said plurality of elongated tubes includes a color-coded portion representing the characteristic impedance of that particular elongated tube.

3. An apparatus in accordance with claim 2 wherein the second sealing means of each of said elongated tubes is color-coded.

4. An apparatus in accordance with claim 1 wherein the partial closure of said second sealing means includes a small diameter passage extending from the tip of the distal end of an elongated tube to the cavity therein.

5. An apparatus in accordance with claim 4 wherein the compliant air cavity provides a parallel hydraulic capacitance and the small diameter passage provides a series hydraulic resistance with respect to said fluid flow system, with the capacitance value determined by the volume of said cavity and the resistance value determined by the diameter and length of said passage.

6. An apparatus in accordance with claim 1 wherein said first sealing means includes a sleeve member extending from the distal end of said elongated tube to facilitate the grasping thereof in inserting and removing it from said inlet port.

7. An apparatus in accordance with claim 1 wherein second sealing means is comprised of an epoxy cement inserted in the distal end of said elongated tube and provided with an orifice therein extending the length thereof.

8. An apparatus in accordance with claim 1 further comprising a multi-position stopcock connected to said inlet port to facilitate the coupling and decoupling of an elongated tube in said fluid flow system.

9. An apparatus in accordance with claim 1 wherein said compliant fluid flow system comprises an electromanometry system with said pressure sensitive means comprising a transducer for measuring hemodynamic pressures.

10. An apparatus in accordance with claim 1 further comprising a threaded coupler for connecting an elongated tube to said inlet port.

* * * * *